United States Patent
Bernhardt et al.

(10) Patent No.: US 7,372,944 B2
(45) Date of Patent: May 13, 2008

(54) X-RAY DIAGNOSTICS DEVICE AND METHOD FOR CONTROLLING AN X-RAY DIAGNOSTICS DEVICE

(75) Inventors: Philipp Bernhardt, Forchheim (DE); Martin Hoheisel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/352,716

(22) Filed: Feb. 13, 2006

(65) Prior Publication Data
US 2006/0182221 A1    Aug. 17, 2006

(30) Foreign Application Priority Data
Feb. 15, 2005   (DE)   ................. 10 2005 006 895

(51) Int. Cl.
*H05G 1/22* (2006.01)
(52) U.S. Cl. ....................... 378/106; 378/108
(58) Field of Classification Search ........... 378/96–97, 378/108–112, 62, 106
See application file for complete search history.

(56) References Cited

U.S. PATENT DOCUMENTS

| | | | |
|---|---|---|---|
| 5,608,775 A * | 3/1997 | Hassler et al. ............. 378/98.8 |
| 6,222,907 B1 | 4/2001 | Gordon, III et al. |
| 6,233,310 B1 * | 5/2001 | Relihan et al. ............. 378/108 |
| 6,295,336 B1 * | 9/2001 | Aach et al. .................. 378/108 |
| 2002/0085672 A1 * | 7/2002 | Ganin et al. ................ 378/108 |
| 2002/0191741 A1 * | 12/2002 | Brendler et al. ............. 378/96 |
| 2005/0238139 A1 * | 10/2005 | Gipp et al. ................... 378/97 |

FOREIGN PATENT DOCUMENTS

| | | |
|---|---|---|
| DE | 44 35 105 A1 | 4/1996 |
| DE | 101 64 170 A1 | 8/2002 |

* cited by examiner

Primary Examiner—Hoon Song

(57) ABSTRACT

The invention relates to an x-ray diagnostics device having an x-ray tube for generating x-rays operated by a high voltage generator, having an x-ray detector for converting incident x-rays into electrical signals, having an image processing system and a control device for the duration of the x-ray pulse, in which parameters of the x-ray diagnostics device can be adjusted, with a computing unit being assigned to the control device, said computing unit determining the spatial frequency-dependent signal-to-noise ratio on the basis of the parameters and calculating therefrom the duration of the x-ray pulse and/or the remaining parameters required for a recording. The invention further relates to a method of this type for controlling the x-ray diagnostics device, in which the duration of the x-ray pulse is controlled such that the recognizability of relevant, moved objects is maximal.

14 Claims, 1 Drawing Sheet

X-RAY DIAGNOSTICS DEVICE AND METHOD FOR CONTROLLING AN X-RAY DIAGNOSTICS DEVICE

CROSS REFERENCE TO RELATED APPLICATIONS

This application claims priority to the German Application No. 10 2005 006 895.2, filed Feb. 15, 2005 which is incorporated by reference herein in its entirety.

FIELD OF INVENTION

The invention relates to an x-ray diagnostics device having an x-ray tube for generating x-rays operated by a high voltage generator, having an x-ray detector for converting incident x-rays into electrical signals, having an image processing system and a control device for the duration of the x-ray pulse, in which the parameters of the x-ray diagnostics device can be adjusted, and to a method for controlling an x-ray diagnostics device of this type.

BACKGROUND OF INVENTION

X-ray systems are generally used in pulsed operation, i.e. the x-ray tube emits an x-ray pulse of a specific duration per image to be recorded. This is particularly advantageous for the display of moved objects. There is thus usually a risk that details of the human body are reproduced blurred, said details being located, image by image, at different positions in the room by heart beats, breathing or other patient movements.

SUMMARY OF INVENTION

A dilemma arises with the search for imaging parameters which result in the best possible recognizability of moved details with a weak image contrast. Although short x-ray pulses result in a slight motion blur in the image, they only deliver a low dose so that the signal-to-noise ratio of the object is low. Longer x-ray pulses allow a higher signal-to-noise ratio, but nevertheless result in blurred details.

The previous method has involved selecting an x-ray pulse with the shortest possible duration. The duration of the x-ray pulse is however also determined by other influences. The dose of the x-ray pulse is controlled via the automatic exposure control (AEC) essentially via the pulse duration. In this case, the adjustment of the tube voltage, the tube current, the filter used and the imaging geometry have a significant influence on the dose so that the pulse duration adjusted by the AEC is not optimal in terms of avoiding motion blurs. The adjustment criteria used to date to design the AEC are frequently of an empirical nature.

U.S. Pat. No. 6,233,310 B1 and U.S. Pat. No. 6,222,907 B1 disclose the automatic determination and adjustment of recording parameters. The movement of the objects to be examined is however not taken into consideration, thereby rendering a minimization of blur artifacts impossible.

FIG. 1 shows a known x-ray diagnostics device which features an x-ray tube 2 supplied by a high voltage generator 1 and generating a radiation beam 3 which penetrates a patient 4 to be examined and strikes an x-ray detector 4 in weakened form according to his transparency, said x-ray detector can be a known solid body flat panel detector for instance. The x-rays converted by the x-ray detector 5 into electrical signals 6 are processed by an image system 7 and displayed on a monitor 8. The x-ray detector 5 or the image system 7 supply an output signal 9 to an automatic exposure control (AEC) 10, said output signal displays a measure for the x-ray dose received by the x-ray detector 5. This is linked to a communication system 11, by means of which control signals are transmitted to the high voltage generator 1, which ensure that the system dose has the desired value.

An object of the invention is to design an x-ray diagnostics device and a method of the type mentioned at the start such that a maximum recognizability of moved details is ensured.

The object is achieved according to the invention for an x-ray diagnostics device such that a computing unit is assigned to the control device, said computing unit determining the spatial frequency-dependent signal-to-noise ratio (S/N) on the basis of the parameter and calculating therefrom the duration of the x-ray pulse and/or the remaining parameters necessary for a recording. This allows moved objects to be optimally recognized.

It has proven advantageous to provide a storage device in which characteristics of the objects to be recorded, such as the motion speed for instance, are stored.

A device for measuring the thickness of an object to be examined can be assigned to the control device in an advantageous manner.

In accordance with the invention the x-ray diagnostics device can feature a filter device which runs in the radiation path of the x-ray tube as a result of the calculation of the computing unit.

The precise motion speed of the object to be examined can be calculated if the x-ray detector's electrical signals of sequential images are supplied to the computing unit, which determines the motion speed therefrom.

Advantageously the adjustable parameters can be tube voltage, tube current, tube pulse duration and/or filter.

According to the invention, the object is achieved for a method in that the duration of the x-ray pulse is controlled such that the recognizability of relevant moved objects is maximal.

In accordance with the invention, the spatial frequency-dependent signal-to-noise ratio can be used as the criterion for the recognizability.

The thickness of the object to be examined which influences the spatial frequency-dependent signal-to-noise ratio can be presumed to be known, determined from the water equivalent of the object or with the aid of a measuring device, with the measuring device being able to determine the thickness by means of mechanical limiters, photo sensors and/or electromagnetic sensors.

The motion speed of the object to be examined which influences the spatial frequency-dependent signal-to-noise ratio can be presumed to be known, assumed as situation-dependent depending on the organ program or determined from the contents of sequential images by image recognition.

BRIEF DESCRIPTION OF THE DRAWINGS

The invention is described in more detail below with reference to an exemplary embodiment shown in the drawing, in which.

DETAILED DESCRIPTION OF INVENTION

Figure 1:
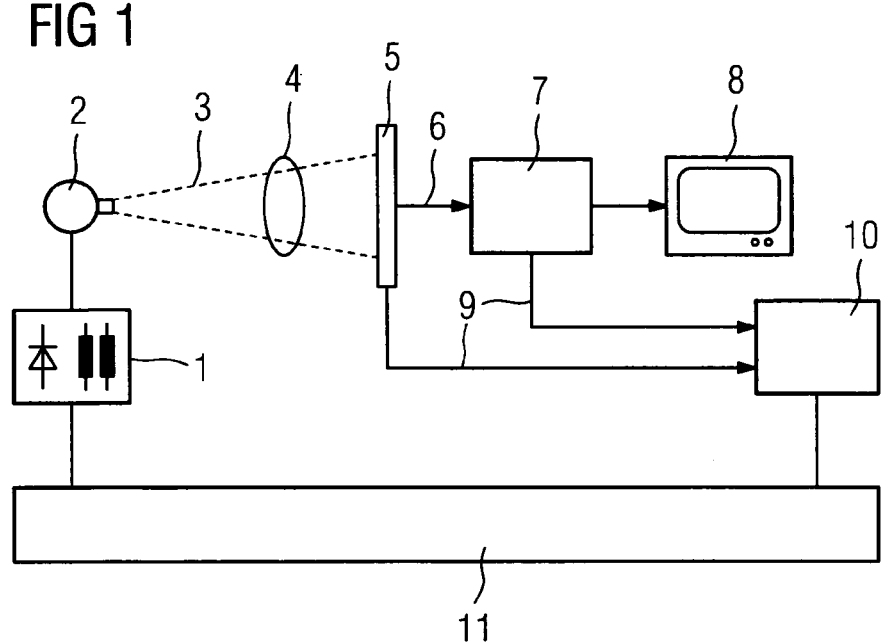
FIG. 1 shows a known x-ray diagnostics device.
Figure 2:
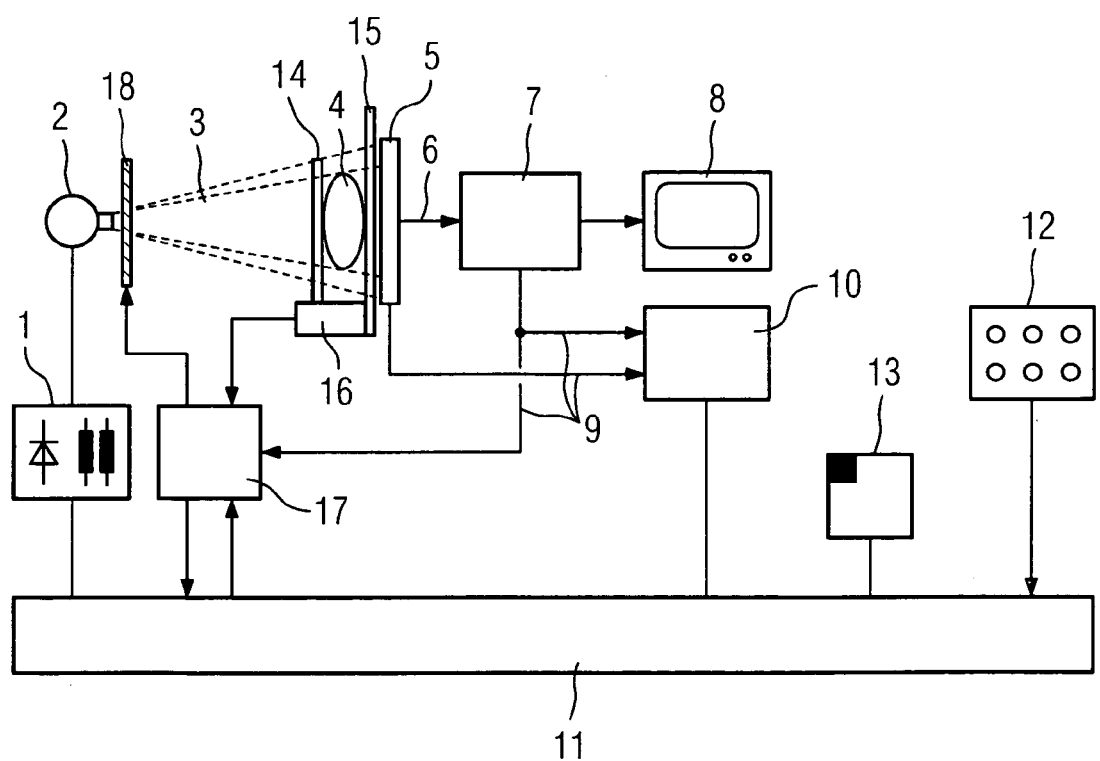
FIG. 2 shows an x-ray diagnostics device according to the invention.

The x-ray diagnostics device 1 to 11 shown in FIG. 2 basically operates as described in FIG. 1. The doctor now enters the desired direction of projection, the distance between x-ray emitter and detector (SID), the organ program etc, via a control panel 12. If the selected organ is known, the typically occurring speeds of the relevant details are also known, which can be stored for instance in a storage device 13.

Since it is desirable for the calculation described further below to know the thickness of the patient, this is determined as far as possible according to one of the following methods. The thickness can be measured for instance on a measuring system 16 with the aid of two limitations 14 and 15, with these limitations possibly being of a mechanical nature, but also being able to be implemented by light sensors, electromagnetic sensors or in another manner. However, the thickness can also be estimated computationally in a known manner from the so-called water equivalent, and the thickness of a water layer with the equivalent x-ray absorption.

The geometric information about the patient 4 is processed in a computing unit 17 together with the other recording parameters of the x-ray system which are transmitted via the communication system 11. The optimal parameters are determined in said computing unit for the x-ray imaging and are transmitted to the high voltage generator 1. Furthermore, the optimal filter 18 resulting from the calculation is moved into the radiation path.

The motion speed of the object to be examined can be automatically calculated online instead of the situation-dependent determination of the motion speed of the object 4 to be examination according to the organ program selected by the control panel 12. For this purpose, the signal 6 is supplied to the computing unit 17, which, by means of image recognition, determines the motion speed from the contents of sequential images.

In a pulsed x-ray system the following parameters are relevant for signal-to-noise ratio (S/N);
  object type (guide wires, stents, vessels filled with contrast means including iodine or $CO_2$, etc.),
  material, geometry and motion speed of the object,
  source-to-image distance (SID),
  geometrical extension factor of the object,
  detector size,
  patient thickness,
  tube voltage U,
  tube current I,
  prefilter, material and thickness and
  exposure time t (pulse duration).

The relationships between these relevant parameters of the x-ray system and the characteristics of the object to be recorded were examined by simulations and it was thus determined that the decisive parameter is the spatial frequency-dependent signal-to-noise ratio, which can be advantageously used to optimize the adjustment parameters of the x-ray system. This allows the best compromise for pulse duration and dose to be found for the recognizability of moved details.

In accordance with the invention, the following should be undertaken:

The object 4 is predetermined, i.e. the body parts of the patient to be examined in the direction of projection desired by the doctor and the relevant organs or other objects in this case, such as the guide wires, catheter and/or stents for instance, are known. If detected quantitatively, this data is entered in the x-ray system via the operating console 12 for instance. The speed is likewise entered, by means of which the relevant objects move in the image plane. This data is buffered in the storage device 13 for instance. Also, the motion speeds can already be stored in a table for the different organs in the storage device 13.

The pulse duration and the remaining recording parameters for the high voltage generator of the x-ray system are now calculated from these specifications, thereby resulting in the best possible visibility of the relevant moved object against the background.

In an extended embodiment variation of this invention, the recorded images are analyzed by means of image recognition in order to determine the speed of the moved objects. The speed determined in this manner is subsequently used to determine the pulse duration and the remaining recording parameters.

The method according to the invention for controlling the x-ray diagnostics device allows the duration of the x-ray pulse to be controlled such that the recognizability of relevant moved objects is maximal, with the spatial frequency-dependent signal-to-noise ratio being able to be used as criteria for the recognizability.

The method according to the invention provides for a set of optimal adjustment values in the complex parameter range of an x-ray system, which makes the moved objects as visible as possible, particularly with weak contrast.

The invention claimed is:

1. An X-ray diagnostics device, comprising:
   an X-ray tube for generating X-rays;
   a high voltage generator for operating the X-ray tube;
   an X-ray detector for converting X-rays received by the detector into electrical signals;
   an image processing system;
   a control device for adjusting a duration of X-ray pulses, the control device configured to adjust a plurality of operating parameters related to operating the X-ray diagnostics device; and
   a computing unit assigned to the control device, the computing unit configured to determine a spatial frequency-dependent signal-to-noise ratio based on the operating parameters, wherein at least one of the following is adjusted by the control device based on the determined spatial frequency-dependent signal-to-noise ratio: 1) time duration of the X-ray pulses and 2) one or more imaging parameters for recording an X-ray image.

2. The X-ray diagnostics device according to claim 1, further comprising a storage device for storing characteristics related to examination objects.

3. The X-ray diagnostics device according to claim 1, further comprising a measuring device assigned to the control device for measuring a thickness of an examination object.

4. The X-ray diagnostics device according to claim 1, further comprising a filter device for moving an optimized filter into a radiation path of the X-ray tube based on a calculation result processed by the computing unit.

5. The X-ray diagnostics device according to claim 1, wherein electrical signals corresponding to sequential X-ray images are fed to the computing unit for determining a motion speed of an examination object.

6. The X-ray diagnostics device according to claim 1, wherein the operating parameters are chosen from the group consisting of a tube voltage, a tube current, an X-ray pulse duration and a filter.

7. A method for controlling an X-ray diagnostics device having
- an X-ray tube for generating X-rays and operated by a high voltage generator;
- an X-ray detector for converting X-rays received by the detector into electrical signals;
- an image processing system; and
- a control device for controlling a duration of an X-ray pulse, the method comprising:
- providing a moving examination object; and
- adjusting the duration of the X-ray pulse such that an X-ray image quality related to an X-ray image recorded from the moving object is maximized, wherein the X-ray image quality is based on a spatial frequency-dependent signal-to-noise ratio, and further wherein at least one of the following is calculated based on the determined spatial frequency-dependent signal-to-noise ratio: 1) time duration of the X-ray pulses, and 2) one or more imaging parameters for recording the X-ray image.

8. The Method according to claim 7, wherein a thickness of the examination object is postulated and used for adjusting the duration of the X-ray pulse without measuring the thickness.

9. The method according to claim 7, wherein a thickness of the examination object is determined from a Water Equivalent of the examination object.

10. The method according to claim 7, wherein a thickness of the examination object is measured and used for adjusting the duration of the X-ray pulse.

11. The method according to claim 10, wherein the thickness is measured by mechanical limiters, light sensors or electro-magnetic sensors.

12. The method according to claim 7, wherein a motion speed of the examination object is postulated without measuring the motion speed.

13. The method according to claim 7, wherein a motion speed of the examination object is determined from an organ program.

14. The method according to claim 7, wherein a motion speed of the examination object is determined by comparing at least two sequential X-ray images recorded from the moving examination object.

\* \* \* \* \*